United States Patent
Gow et al.

(10) Patent No.: US 7,105,185 B2
(45) Date of Patent: Sep. 12, 2006

(54) KAVALACTONE PROFILE

(75) Inventors: Robert Gow, Naples, FL (US); John Pierce, Moreno Valley, CA (US); Brian Pierce, Moreno Valley, CA (US); William Birdsall, Naples, FL (US)

(73) Assignee: HerbalScience, LLC, Naples, FL (US)

( * ) Notice: Subject to any disclaimer, the term of this patent is extended or adjusted under 35 U.S.C. 154(b) by 424 days.

(21) Appl. No.: 10/273,943

(22) Filed: Oct. 18, 2002

(65) Prior Publication Data

US 2004/0072897 A1 Apr. 15, 2004

Related U.S. Application Data

(63) Continuation-in-part of application No. 10/263,579, filed on Oct. 3, 2002.
(60) Provisional application No. 60/369,889, filed on Apr. 3, 2002, and provisional application No. 60/326,928, filed on Oct. 3, 2001.

(51) Int. Cl.
*A61K 32/78* (2006.01)

(52) U.S. Cl. ............... 424/734; 424/725; 424/773
(58) Field of Classification Search ............. 424/195.1, 424/725, 734, 773
See application file for complete search history.

(56) References Cited

U.S. PATENT DOCUMENTS

| | | | |
|---|---|---|---|
| 4,154,823 A | 5/1979 | Schutt | |
| 4,248,861 A | 2/1981 | Schutt | |
| 5,178,735 A | 1/1993 | Manabe et al. | |
| 5,234,947 A | 8/1993 | Cherksey | |
| 5,273,754 A | 12/1993 | Mann | |
| 5,296,224 A | 3/1994 | Schwabe | |
| 5,380,826 A | 1/1995 | Castor et al. | |
| 5,401,502 A | 3/1995 | Wunderlich et al. | |
| 5,440,055 A | 8/1995 | Castor | |
| 5,466,455 A | 11/1995 | Huffstutler, Jr. et al. | |
| 5,512,285 A | 4/1996 | Wilde | |

(Continued)

FOREIGN PATENT DOCUMENTS

| | | |
|---|---|---|
| EP | 987026 | 3/2000 |
| GB | 943121 | 11/1963 |
| WO | WO 99/61038 | 12/1999 |
| WO | WO00/72861 | 7/2000 |

OTHER PUBLICATIONS

Ashraf–Khorassani et al. Supercritical Fluid Extraction of Kava Lactones from Kava Root and their Separation Via Supercritical Fluid Chromatography; Chromatographia vol. 50, No. 5/6, Sep. 1999, pp. 287–292.*

(Continued)

*Primary Examiner*—Patricia Leith
(74) *Attorney, Agent, or Firm*—Troutman Sanders LLP

(57) ABSTRACT

A method of producing a processed kava product involves using an extraction solvent, such as liquid $CO_2$, to preferentially extract different kavalactones from the source material at different rates. By controlling the extraction parameters and stopping the extraction before all of the kavalactones have been extracted or allowing the extracted kavalactones to be preferentially precipitated in one or more collection environments, a processed kava product can be produced that has a kavalactone distribution profile that can differ substantially from that of the source material. As a result, roots from a less desirable kava cultivar can be used to produce a processed kava product which has a kavalactone distribution profile that is similar to that of a highly desired cultivar. A material having a preferred kavalactone distribution profile is also disclosed. The kava paste can be further processed to produce a dry flowable powder suitable for use in, e.g., a tableting formula. A rapid dissolve tablet formulation for use in the delivery of kavalactones is also disclosed.

13 Claims, 7 Drawing Sheets

Methysticin + Dihydromethysticin Weight Percentages Measured in the Lateral Roots for Five Usage Classes of Vanuatu Kava Cultivars: Daily, Custom, Two-day, Medicinal and No Drink

U.S. PATENT DOCUMENTS

| | | | |
|---|---|---|---|
| 5,554,382 | A | 9/1996 | Castor |
| 5,578,307 | A | 11/1996 | Wunderlich et al. |
| 5,585,386 | A | 12/1996 | Rosenbaum |
| 5,639,441 | A | 6/1997 | Sievers et al. |
| 5,698,199 | A | 12/1997 | Mori et al. |
| 5,750,709 | A | 5/1998 | Castor |
| 5,770,207 | A * | 6/1998 | Bewicke .................. 424/734 |
| 5,776,486 | A | 7/1998 | Castor et al. |
| 5,776,935 | A | 7/1998 | Danysz et al. |
| 5,821,450 | A | 10/1998 | Fedida |
| 5,854,064 | A | 12/1998 | Castor et al. |
| 5,877,005 | A | 3/1999 | Castor et al. |
| 5,891,465 | A | 4/1999 | Keller et al. |
| 5,906,825 | A | 5/1999 | Seabrook, Jr. et al. |
| 5,906,848 | A | 5/1999 | Kreuter et al. |
| 5,976,550 | A | 11/1999 | Engel et al. |
| 5,977,120 | A | 11/1999 | Giles, Jr. |
| 6,024,998 | A | 2/2000 | Kreuter et al. |
| 6,025,363 | A | 2/2000 | Giles, Jr. |
| 6,045,825 | A | 4/2000 | Cody |
| 6,068,846 | A | 5/2000 | Cho et al. |
| 6,080,410 | A | 6/2000 | Bewicke |
| 6,095,134 | A | 8/2000 | Sievers et al. |
| 6,117,431 | A | 9/2000 | Ramazanov et al. |
| 6,143,300 | A | 11/2000 | Stevenot |
| 6,159,473 | A | 12/2000 | Watkins et al. |
| 6,174,542 | B1 | 1/2001 | Hinton et al. |
| 6,207,164 | B1 | 3/2001 | Kreuter et al. |
| 6,238,696 | B1 | 5/2001 | Wang |
| 6,238,722 | B1 | 5/2001 | Meadows |
| 6,241,988 | B1 | 6/2001 | Erdelmeier et al. |
| 6,277,396 | B1 | 8/2001 | Dente |
| 6,280,736 | B1 | 8/2001 | Erdelmeier et al. |
| 6,288,109 | B1 | 9/2001 | Chatterjee et al. |
| 6,290,985 | B1 | 9/2001 | Ream et al. |
| 2003/0180395 | A1 * | 9/2003 | Bueter .................. 424/725 |

OTHER PUBLICATIONS

Boonen et al. Contribution to the Quantitative and Enantioselective Determination of Kavapyrones by High–Performance Liquid Chromatography . . .; Journal of Chromatography, B: Biomedical Sciences and Applications (1997) 702(1+2), pp. 240–244.*

Boonen et al. Influence of Genuine Kavapyrone Enantiomers on the GABAA Binding Site; Planta Medica (1998), 64 (6), pp. 504–506.*

Ganzera et al. Analytical Techniques for the Determination of Lactones in Piper Methysticum Forst.; Chromatographia (1999), 50 (10/11) pp. 649–653.*

Segoet–Kujawa et al. Isolation of Kava–Lactones by Rotatory Thin Layer Chromatography; Herba Polonica (1999) vol. 45, No. 3, pp. 186–191.*

Uebelhack et al. Inhibition of Platelet MAO–B by Kava Pyrone–Enriched Extract from Piper Methysticum Forster (Kava–Kava); Pharmacopsychiatry (1998), 31 (5), pp. 187–192.*

Cappaso, A. et al., Experimental Investigations of the Synergistic–Sedative Effect of Passiflora and Kava, Acta Therapeutica 21, 1995, pp. 127–140, vol. 21, No. 2.

Kubatova, Alena et al., Comparison of Subcritical Water and Organic Solvents for Extracting Kava Lactones from Kava Root, Journal of Chromatography, Jul. 20, 2001, pp. 187–194. vol. 923., No. 1–2. Elsevier Science Publishers B. V. Amsterdam, NL.

Rex, Andre et al., Anxiolytic–Like Effects of Kava–Kava in the Elevated Plus Maze Test–A Comparison with Diazepam, Progress in Neuro–Psychopharmacology & Biological Psychiatry, Jun. 2002, pp. 855–860, vol. 26, No. 5.

Williamson, E.M., Synergy and Othe rInteractions in Phytomedicines, Phytomedicine, Sep. 2001, pp. 401–409, vol. 8, No. 5.

Avila et al., Supercritical Fluid Extraction of Kava Lactones from Piper Methysticum (Kava) Herb, Midwest Research Institute, vol. 20, Oct. 1997.

Khorassani et al., Supercritical Fluid Extraction of Kava Lactones from Kava Root and Their Separation Via Supercritical Fluid Chromatography, Chromatographia, vol. 50, Sep. 1999.

Uy Nguyen et al., Extraction and Fractionation of Spices Using Supercritical Fluid Carbon Dioxide, Presented at 5th International Symposium on Supercritical Fluids, 1998.

* cited by examiner

ND PROCESSED KAVA PRODUCTS PRODUCED USING THE SAME", filed Oct. 3, 2002, which claimed priority under 35 U.S.C. § 119 to U.S. Provisional Patent Application Ser. No. 60/326,928 entitled "Methods For Processing Kava Root (Piper Methysticum) And Kava-Derived Products Generated By These Methods Having Controllable Kavalactone Ratios", filed on Oct. 3, 2001, and U.S. Provisional Application Ser. No. 60/369,889 entitled "Dry Flowable Kava Extract Powder And Fast-Dissolve Kava Extract Composition For Oral Delivery", filed on Apr. 3, 2002. The entire contents of these applications are hereby expressly incorporated by reference.

FIELD OF THE INVENTION(S)

This invention is related to methods for processing kava to produce a kava extract with particular kavalactone concentration profile, a processed kava product, such as a dry flowable kava extract powder, and the use of such a powder in a rapid-dissolve tablet for oral delivery. Furthermore, this invention relates to a particular kavalactone concentration profile.

BACKGROUND

Kava plants, a type of pepper plant also known as Piper methysticum, are generally found in Polynesia, Melanesia, and Micronesia. The kava plant contains high concentrations of kavalactones (sometimes referred to as kavapyrones), including kavain, methysticin, yangonin, dihydromethysticin, desmethoxyyangonin, and dihydrokavain, and has been used as an herbal medicine. The prized part of the kava plant is the root system because it contains the highest concentrations of the active kavalactones. Kavalactones are also found in other parts of the plant. General information about kava plants can be found in Vincent Lebot, et al., "*Kava The Pacific Elixir, The Definitive Guide to its Ethnobotany, History, and Chemistry*", Inner Traditions Intl. Ltd. (March 1997).

After a kava plant is harvested, the root is conventionally processed to generate a consumable product. In conventional and historical methods, the root is dried and ground to a powder. This powder contains not only the kavalactones but also plant oils, resins, and other substances. The powder can be mixed with water to form a beverage. The resinous ground dried root can also be packaged into capsules or other forms of delivery.

The effects of ingesting kava root extract will vary from person to person. Common effects include a state of relaxation and a reduction in muscle tenseness. Kava root has also been used to help sufferers of insomnia. It can also produce a mild state of euphoria. The ratios of the various kavalactones in the consumed product has a large impact on the effect experienced by the user.

There are a large number of different kava cultivars, each of which has differing ratios of the different kavalactones. Through historical knowledge and experimentation, various kava cultivars have been classified according to their effect, such as "daily" or "one-day", "custom", "two-day", "medicinal", and "no drink". "Daily" kava cultivars are generally consumed daily and have relatively short-term effects. "Custom" kava cultivars tend to be used for ritual and ceremonial purposes. "Two-day" kava cultivars tend to have pronounced physiological effects and are known as "two day" because the drinker is usually affected for two days. "Medicinal" kava cultivars are specific for the treatment of ailments like rheumatism. "No Drink" kava cultivars are not recommended for consumption because they tend to induce nausea and other undesirable effects.

More recently, there have been concerns associating kava with occurrences of liver damage, although these reports are primarily anecdotal. Studies done in the 1970s and 1980s have found that "two day" kava cultivars have particularly high concentrations of methysticin and dihydromethysticin. These kavalactones contain a methylenedioxyphenyl functional group which, when activated through metabolic activity, forms intermediary compounds that can inactivate multiple P450 enzymes. There are some suggestions that inhibition of P450 enzymes can interfere with the metabolism of many pharmaceuticals. The solution proposed in the prior art is the development of new kava cultivars with reduced amounts of methysticin and dihydromethysticin and increased kavain content.

One of the most highly prized kava cultivars is a one-day cultivar that grows in Vanuatu. Relative to other cultivars, this cultivar is naturally low in methysticin and dihydromethysticin and has a proportionally higher concentration of kavain. However, this cultivar is not widely grown or available and most commercially available cultivars have increased levels of methysticin and dihydromethysticin and lower concentrations of kavain. Although breeding of new cultivars that can be widely grown and which have lower concentrations of methysticin and dihydromethysticin and increased concentrations of kavain is possible, this can be a time consuming process and is not assured of success. In addition, the kavalactones suspected of producing toxic effects when consumed by humans are also toxic to various insects and microorganisms, such as fungi. Thus, the hardiest cultivars are generally those which are least suitable for human consumption.

In a kava extraction process, the rate at which various kavalactone components are extracted varies according to the extraction solvent and extraction conditions used. However, kava root extracts are conventionally sold based upon total kavalactone content. Thus, the focus of conventional commercial extraction techniques has been to extract as much of the kavalactone content from the root source as possible and knowledge regarding different rates of extraction for different kavalactones is used to adjust the extraction process or select appropriate extraction steps to provide for the greatest total kavalactone extraction.

Various extraction techniques have been used to process kava root. Such techniques include the use of supercritical carbon dioxide ($CO_2$) extraction, fluorocarbon extraction, and the use of various other organic and non-organic solvents to remove the kavalactones from the dried root. The resulting bulk extract is in the form of a paste.

Supercritical $CO_2$ processes have been found to extract the largest quantity of kavalactones from the root and thus conventional practice has been to focus on the use of supercritical $CO_2$ to extract all of the kavalactones from the root in the production of kava extracts. As will be appreciated, bulk extracts of substantially all of the kavalactones in the root will generally contain kavalactones in the same or nearly the same proportions as present in the source root. Because of the differing effects produced by variations in the kavalactone ratios of different cultivars, producers of such kava products are limited to specific kava cultivars as source materials in order to produce a kava product that produces a desired effect.

To the extent that the distribution profile of the various kavalactones in the extract have been of concern, conventional practice is to use additional processing steps, such as high pressure liquid chromatography (HPLC), to extract individual kavalactones. For example, HPLC and other chromatographic techniques, such as "flash" chromatography, have been used to process bulk kava extracts to isolate individual kavalactones. This process is cumbersome to implement and requires the use of machinery that is bulky and expensive to operate. Methods for extracting and purifying kava, including supercritical $CO_2$ extraction and chromatography, are discussed in PCT publication WO 00/72861 to Martin et al. entitled "Pharmaceutical Preparations of Bioactive Substances Extracted from Natural Sources."

It would be advantageous and is an object of the present invention to provide a method of processing kava to provide an extract of kava as a paste, powder, or in other forms, and which allows the kavalactone profile to be altered during processing so as to have reduced levels of methysticin and dihydromethysticin and increased levels of kavain and dihydrokavain. It would be additionally advantageous if such techniques allowed the production of a processed kava product that had a kavalactone profile similar to (or improved upon) that of the most preferred "one-day" cultivars from Vanuatu by using a kava feedstock from a less desired cultivar. There would be yet a further advantage if such an altered-profile kava product could be produced using a minimal number of processing steps and without requiring additional processing, such as via chromatography, to isolate each individual kavalactone from the extract and then recombine the isolated kavalactones as appropriate. Still another advantage would be artificially producing a material having a desired kavalactone profile.

There has been widespread use of bulk kava paste extracts as dietary supplements, e.g., mixed in drinks or packaged in capsules. Because kava paste is not always well suited for processing into consumable form or for distribution, e.g., as a dietary supplement, it would also be advantageous to produce a dry flowable kava powder. The powder can be distributed as is or further processed, e.g., to produce kava tablets.

When consumed, kava is typically swallowed. The kavalactones then pass through the stomach and intestines as they are absorbed into the bloodstream. It can take a relatively long time for the body to process kava and the effect of the ingested kavalactones can then be further diminished as the compounds are processed by the liver. It would therefore also be advantageous to deliver kava in the form of a rapid-dissolve tablet which would permit the kavalactones to be absorbed orally.

SUMMARY OF THE INVENTION(S)

These and other objectives are met by use of the present methods of processing kava to produce a kava product, such as a paste, resin, oil, or a powder suitable for use in a fast dissolve tablet and other applications, and which as a kavalactone profile that is altered from the profile of the kava feedstock. The present methodologies also allow the distribution of kavalactones to be altered or adjusted to achieve a particular kavalactone profile wherein the effectiveness of the kava can be enhanced or the negative effects reduced. Various other novel kava extract compositions are also presented.

Preferably, a two stage process is used. First, the kavalactones are extracted from the kava root material to form a kava paste. Preferably, the paste is generated using liquid $CO_2$ extraction techniques. However, under some conditions, supercritical $CO_2$ extraction techniques can be used. During processing, an initial pressurization/depressurization step can also be included to increase the rate at which the kavalactones can be extracted from the rootstock. The output of the first processing step is a viscous paste, oil, and/or resin.

The paste can then be subjected to a second or further refinement stages, if desired, to further purify the kavalactones and produce a highly refined paste extract. Preferably, the parameters of the second processing stage (and possibly the first stage as well) are selected to alter the kavalactone distribution in the raw material in order to achieve a predetermined distribution and concentration of the various kavalactones without the need of chromatography or other techniques conventionally used to extract individual kavalactones.

Advantageously, the use of the extraction techniques according to the various embodiments of the invention thus allows high quality kavalactone having a desired profile, such as reduced levels of methysticin and dihydromethysticin and increased levels of kavain and dihydrokavain, to be easily and economically produced from a kava feedstock, such as dried ground root, which has an undesired kavalactone profile. In a particular example, an undesired kava stock, such as a "two-day" or "no-drink" cultivar, can be processed to produce a kava extract having a kavalactone distribution profile which is comparable to the most desired "one-day" Vanuatu cultivar.

For example, processing of kava using $CO_2$ at pressures of 1100 psi or greater and at a temperature greater than 31° C. places the $CO_2$ in a supercritical state and will extract on the order of 80% to 100% of the kavalactones in the source. However, the extraction rate of the various kavalactones are fairly similar and the resulting extract will have a kavalactone profile that is similar to, if not identical to, that of the feedstock. (However, with careful control over the extraction parameters, subtle changes in the kavalactone profile can be made using supercritical $CO_2$ extraction.)

In contrast, it has been found that processing the kava feedstock using liquid $CO_2$ at pressures of between about 1100 psi to about 1800 psi and temperatures between about 0° C. and about 25° C. produces preferential extraction wherein methysticin and dihydromethysticin are extracted at a considerably slower rate than other kavalactones. It has been further found that processing at between about 1100 to about 1500 psi at temperatures between about 5° C. and about 10° C. also produces an increased relative concentrations of kavain and dyhydrokavain relative to other kavalactones in the extract.

Through use of the present techniques, kava extracts can be produced having a kavalactone profile that is unlike those found in nature and the profile can be tailored to meet particular design considerations. Preferably, the kava product has kavalactone properties that have been selected to be low in the combined weight percentage of methysticin (M) and dihydromethysticin (DHM), low in the combined weight percentage of desmethoxy yangonin (DMY) and yangonin (Y), and high in the combined weight percentage of kavain (K) and dihydrokavain (DHK). The preferred kava product can be characterized according to one or more of the following attributes: (a) a combined weight percentage of the six major kavalactones methysticin (M), dihydromethysticin (DHM), yangonin (Y), desmethoxyyangonin (DMY), kavain (K), and dihydrokavain (DHK) of between about 20% to a maximum of about 90%; (b) a combined weight percentage of M and DHM between about 5–15% to about 29%; (c) a ratio of Y to DMY by weight, expressed as the logarithmic function 10* LOG10(Y/DMY) in dB units, from about −1 to about 2; (d) a ratio of DHK to K by weight, expressed as the logarithmic function 10*LOG10(DHK/K) in dB units, from about −4 to about 1; (e) a combined weight percentage of Y and DMY between about 5% to about 20–25%, and (f) a combined weight percentage of flavokavain A and flavokavain B of between about 0.3% to about 3%.

Alternatively, the kava product may be synthetically produced by combining the particular kavalactones in the desired weight ratios. The resulting material preferably has a kavalactone profile having at least one of the following characteristics: a) a combined weight percentage of M and DHM less than about 15% of the total weight of the profile, b) a combined weight percentage of DMY and Y less than about 8% of the total weight of the profile and c) a combined weight percentage of K and DHK is greater than about 70% by weight of the kavalactone profile.

Once a suitable kava paste, resin, or oil, is provided, it can then processed for various uses. For direct ingestion, for example, a paste can be sweetened and flavored. In addition or alternatively, the paste can be mixed with other dietary supplements, such as the very sweet tasting herb *Stevia*, or other herbal or non-herbal ingredients.

A kava paste can also be further processed to prepare a high quality dry flowable powder which can be used, for example, to produce an ingestible kava tablet. In a first embodiment, a kava paste is combined with a carrier, such as maltodextrin, dextrose, or starches and mixed with a suitable solvent, such as ethyl alcohol or water. The mixture is then spray dried to produce a powder having grains comprised of kava extract and the carrier. In a second embodiment, an emulsion of kava paste is formed in water or ethyl alcohol using, e.g., magnesium carbonate, magnesium carbonate+silica (at up to about 2% by weight), whey protein, maltodextrin, carboxymethylcellulose and/or other suitable materials. The emulsion is then dried and powdered. In a third embodiment, the extract is processed with supercritical $CO_2$ and a carrier, such as maltodextrin, dextrose, or starches and then subjected to a rapid decompression of the supercritical fluid. As the fluid evaporates, the extract and kava are deposited as micro-sized particles.

The resulting powder, preferably having a preselected ratio of kavalactones, can then be formed into a tablet that, when placed in the mouth, dissolves rapidly over a period of between about 5 to about 180 seconds and preferably in about 15 to about 60 seconds. A tableting powder can be formed by combining between about 25% to about 60% by weight of the powdered kava extract with between about 30% to about 60% by weight of a dry water-soluble absorbant such as magnesium carbonate, or a diluent, such as lactose. Other dry tablet additives, such as one or more of a sweetener, flavoring and/or coloring agents, a binder, such as acacia or gum arabic, a lubricant, a disintegrant, and a buffer, can also be added to the tableting powder. Preferably, the dry ingredients are screened to a particle size of between about 80 to about 100 mesh.

To form the tablets, the tableting powder is then wet with a solvent, such as alcohol or water, until it achieves a doughy consistency. The paste is then molded or pressed into tablets which are dried and packaged. The tablets can be of any suitable size, shape, and weight. Preferably, the tablets are formed into disks or wafers having a diameter of between about ⅛ and about ½ inch, a thickness of between about 0.08 and about 0.2 inch, and a weight of between about 50 mg to about 1000 mg. The tablets are preferably homogeneous. However, they can also be formed of regions of kava extract composition separated by non-kava extract regions in periodic or non-periodic sequences as may be desired.

BRIEF DESCRIPTION OF THE DRAWINGS:

The following detailed description of the preferred embodiment(s) will be better understood with reference to the following figures in which.

DESCRIPTION OF THE PREFERRED EMBODIMENT(S)

To better appreciate the utility of the present invention, it is useful to present data describing the differences between the total and relative amounts of various kavalactones in a variety of kava cultivars. The HPLC measurements for kava cultivars are taken from V. Lebot's and J. Levsque's paper in *Allertonia* (1989) entitled, "On The Origin And Distribution Of Kava (*piper methysticum* forst. F., *piperaceae*): A Phytochemical Approach". Lebot's and Levesque's procedure for the extraction and analysis of total kavalactone weight percentages and kavalactone concentration spectra for kava cultivars consisted of the following steps: First, select only the lateral roots of a kava plant that reached the age of two years. Next, dry lateral roots in an oven at 60–80° C. for eight hours, and then grind the roots into powder. Then, perform a six hour Soxhlet extraction of powdered root using chloroform as the solvent. Finally, analyze the chloroform extract using HPLC.

Note that Lebot and Levesque used only the lateral roots to measure the kavalactone concentration spectrum for a given kava cultivar. This is important because different parts of the kava plant (e.g., rhizome, stem, leaves) have different kavalactone concentration spectra, as well as different total kavalactone weight percentages. Total kavalactone weight percentage is highest in the lateral roots, and decreases towards the aerial parts of the plant (pg. 67, Lebot, Merlin, Lindstrom, *Kava—The Pacific Elixir,* 1997). Lebot (1988) found in Vanuatu kava cultivars that when the total kavalactone weight percentage was about 15% in the lateral roots, it dropped to about 10% and 5% in the rhizome and basal stem, respectively. Lebot, et al (1997) on pp. 74–75 report that K and DMY are the dominant kavalactones in the rhizome, whereas DHK and DHM tend to be the kavalactones with the highest concentrations in the leaves. In summary, the kavalactone concentration spectrum and total kavalactone weight percentage for a given kava cultivar can be determined by a number of factors, which include age of the plant, method of extraction, as well as the part of the plant.

66 of the 67 Vanuatu cultivars identified in Table 2 in Lebot and Levesque (1989) were analyzed (33 Daily, 11 Custom, 14 Two-day, 4 Medicinal, and 4 No Drink cultivars). Also analyzed were 26 of the 27 Fijian kava cultivars from Table 6 in Lebot and Levesque (1989). Lebot and Levesque did not classify these cultivars according to the system described above. HPLC was used to determine the total kavalactone weight percentages and kavalactone concentration spectra for the various samples.

Figure 1:
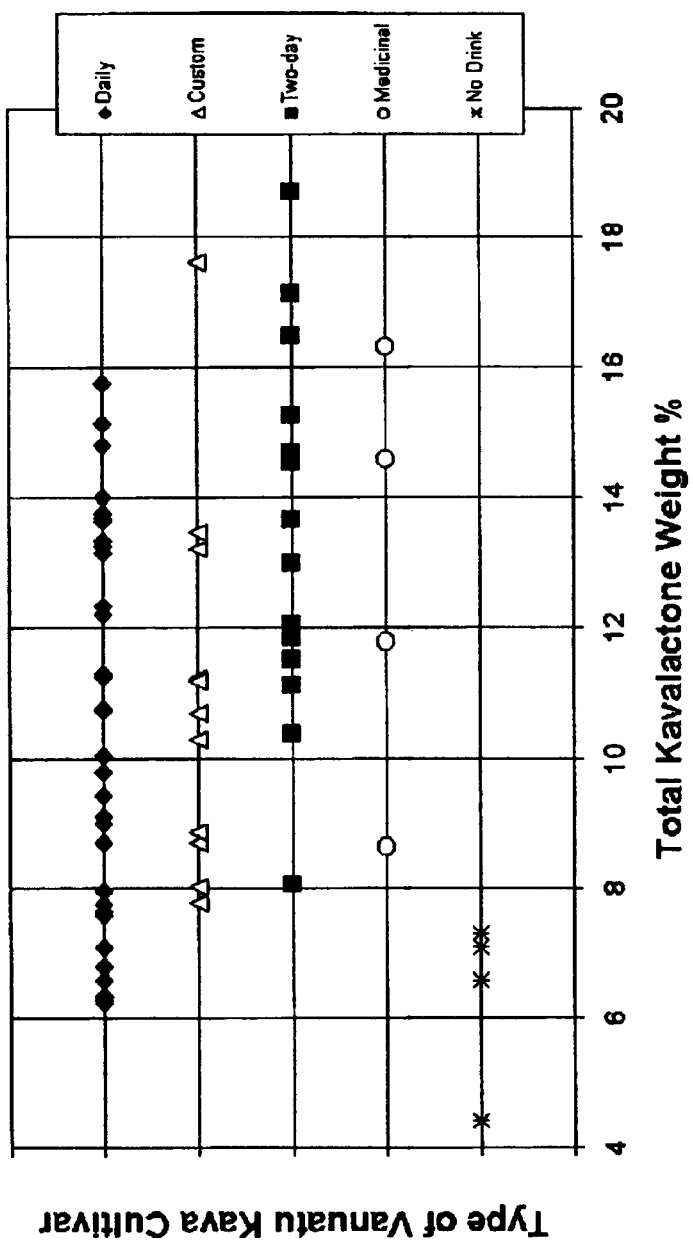
FIG. 1 is a plot of total kavalactone weight percentages measured in the lateral roots for five usage classes of Vanuatu kava cultivars: Daily, Custom, Two-day, Medicinal and No Drink.

FIG. 1 presents a plot of the total kavalactone weight percentages measured by Lebot and Levesque (1989) in the lateral roots for the five usage classes of Vanuatu kava cultivars: Daily (D), Custom (C), Two-day (T), Medicinal (M), and No Drink (N). As will be appreciated, the total kavalactone weight percentage does not uniquely identify the type of kava cultivar, e.g., there are several D, C, T and M kava cultivars with total kavalactone weight percentages in the range of 11–12%. FIG. 1 also shows that the selection of a kava cultivar with a very low total kavalactone percentage does not mean that it has the least effect because the class of No Drink kava cultivars has the lowest average total kavalactone concentration. Accordingly, kava cultivars that have high concentrations of desirable kavalactones may also contain high concentrations of undesirable kavalactones, making these cultivars unsuitable for use in producing consumable kava products without first altering the profile of the kavalactones.

Figure 2:
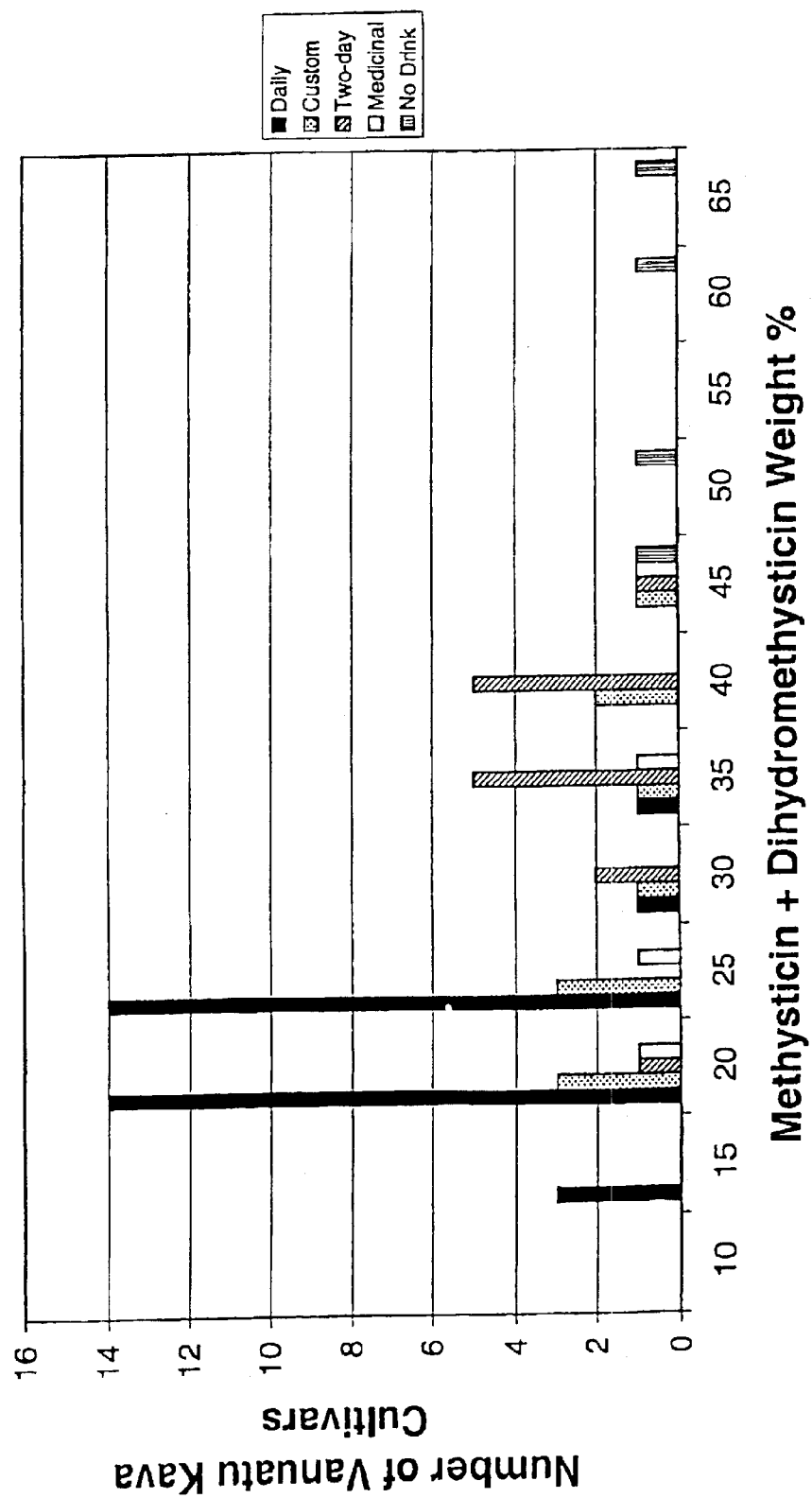
FIG. 2 is a plot of Methysticin+dihydromethysticin weight percentages measured in the lateral roots for five usage classes of Vanuatu kava cultivars.

FIG. 2 is a bar graph plotting number of Vanuatu kava cultivars vs. the combined M+DHM weight percentage measured by Lebot and Levesque (1989) in the lateral roots for the D, C, T, M and N classes of kava cultivars described for FIG. 1. Table 1 below summarizes the M %+DHM % averages for the five usage classes:

TABLE 1

Average Weight Percentage of Methysticin and Dihydromethysticin in Lateral Roots for the Five Usage Classes of Vanuatu Kava cultivars

| Kava Cultivar Usage Class | Average M % + DHM % |
| --- | --- |
| Daily | 25 ± 4% |
| Custom | 33 ± 9% |
| Two-day | 39 ± 6% |
| Medicinal | 33 ± 13% |
| No Drink | 57 ± 10% |

FIG. 2 and Table 1 indicate that the frequency of use for a kava cultivar is proportional to the M %+DHM %, with the Daily kavas having the lowest average of 25±4%, the Two-day kavas are 14% higher at 39±6%, and the No Drink kavas have the highest M %+DHM % at 57±110%. Thus, the higher the M %+DHM % for a Vanuatu kava cultivar, the less frequent its use.

Moreover, M %+DHM % has been found to be proportional to the degree of induced nausea, which could help explain why frequency of use drops with increasing M %+DHM %. In particular, Lebot, et al (1997) report on pg. 78 that DHM is a major component of Two-day (or *tudei*) kavas that frequently produce nausea. According to the work of the Meyer group in Freiburg, the M and DHM kavalactones are absorbed the slowest in the gastrointestinal tract. The strong anticonvulsive and muscle relaxant action of M and DHM (see Meyer group work) combined with the fact that M and DHM remain for longer periods of time in the gastrointestinal tract are consistent with the induction of nausea resulting from kava preparations containing high percentages of M and DHM.

The relationships between M %+DHM % and Vanuatu kava cultivar usage presented in FIG. 2 and table 1 above are important steps in classifying Vanuatu kava cultivars, and can also be used to classify other kava preparations and products. However, this classification does not help with distinguishing the neuroactive effects of the different kava cultivars. In order to better distinguish the neuroactive effects of kava products, a two-dimensional logarithmic coordinate system is presented which maps the concentrations of the neuroactive kavalactones that cross the blood-brain barrier the fastest: K, DHK, Y and DMY. The Y/DMY ratio defines the "X-axis" for this coordinate system and the DHK/K ratio defines the "Y-axis". The logarithmic nature of the coordinate system comes from the fact that the DHK/K and Y/DMY concentration ratios are in dB's, which means $10^* \, LOG_{10}(DHK/K)$ and $10^* \, LOG_{10}(Y/DMY)$. A point centered on the origin (0,0) signifies that the DHK/K and Y/DMY ratios are both 1. Positive values reflect ratios greater than 1, and negative values correspond to ratios less than 1.

Figure 3:
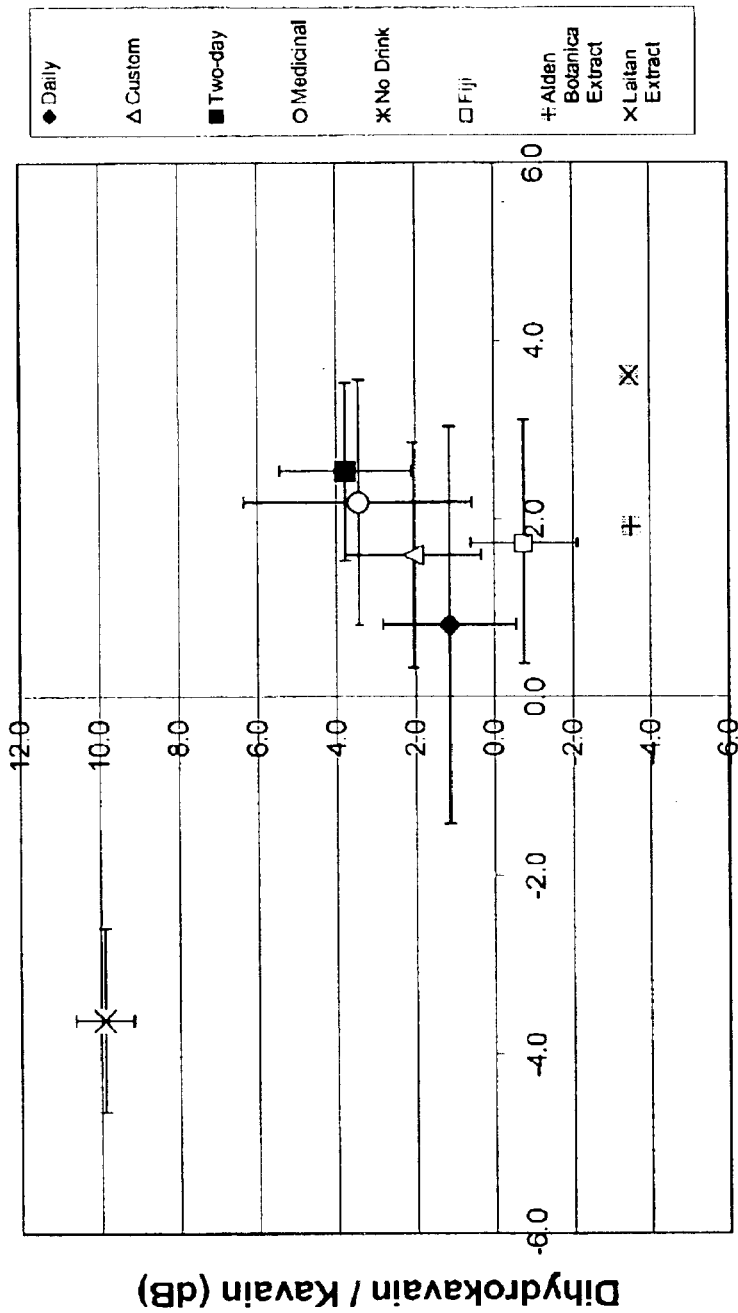
FIG. 3 is a plot of average dihydrokavain+kavain vs. yangonin+desmethoxyyangonin kavalactone concentration ratios measured in the lateral roots for various kava cultivars and extracts.
Figure 4:
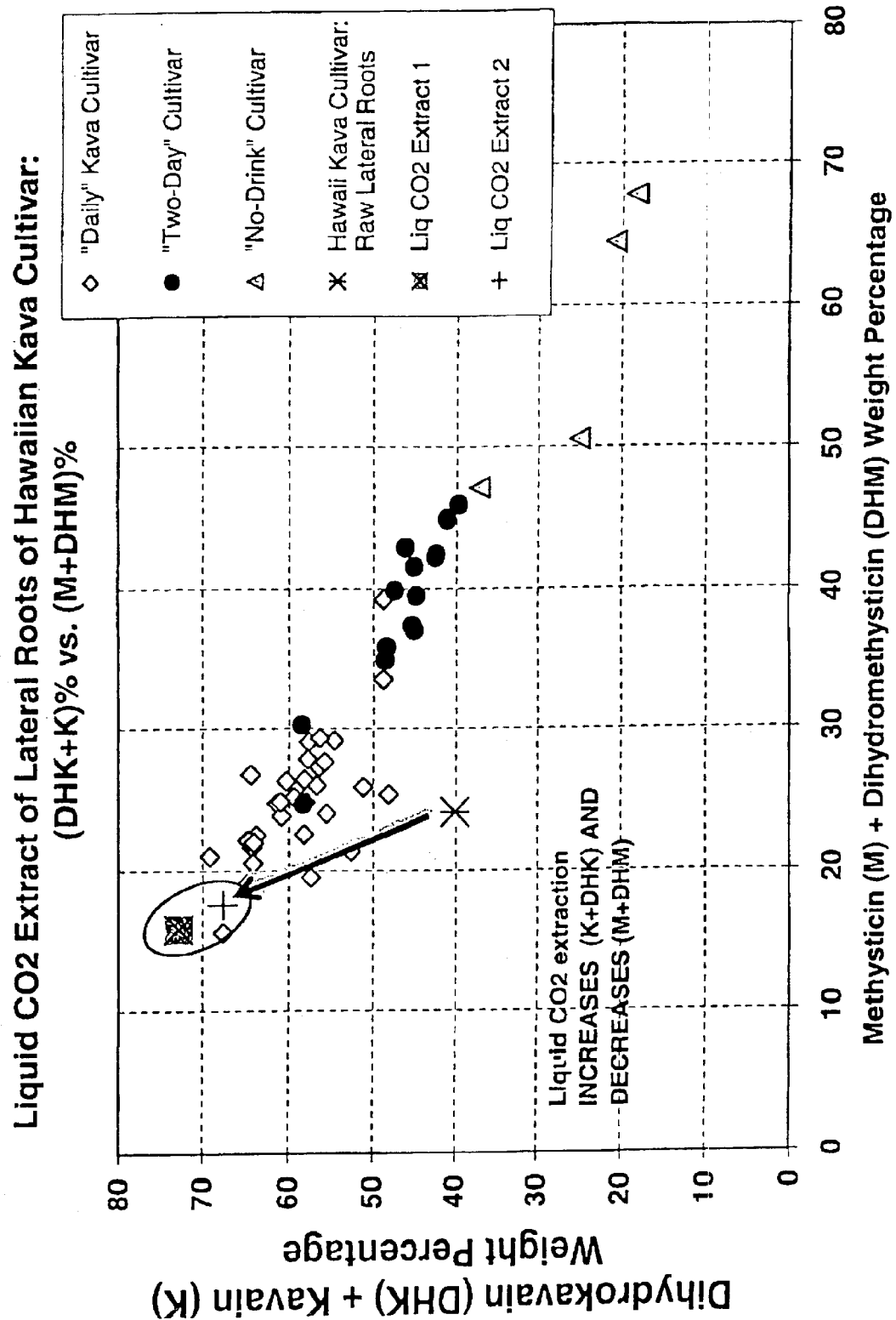
FIGS. 4–7 show plots of relative kavalactone concentrations for different kava cultivars and show changes in the kavalactone profile introduced during processing according to the present invention.
Figure 5:
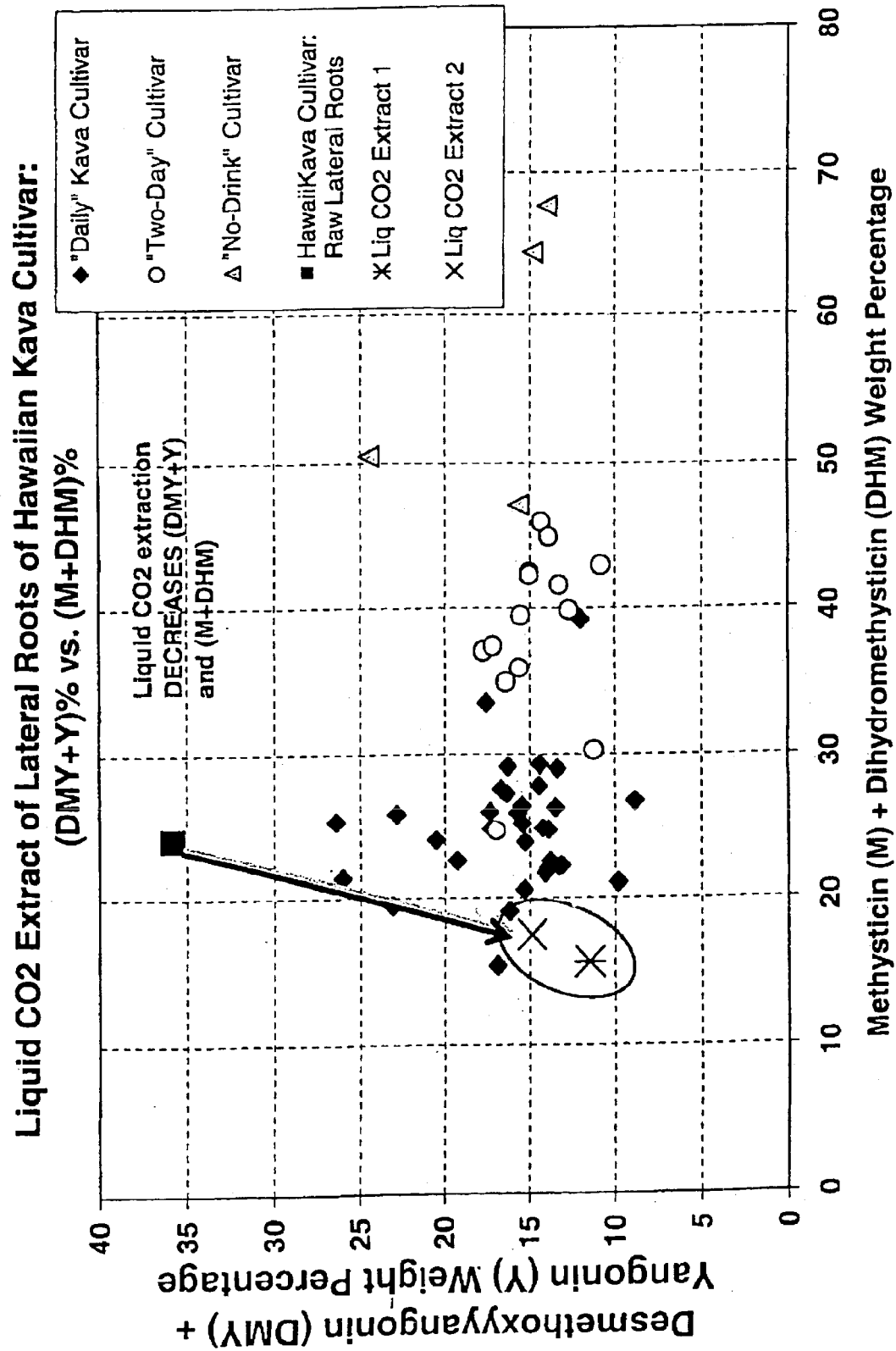
Figure 6:
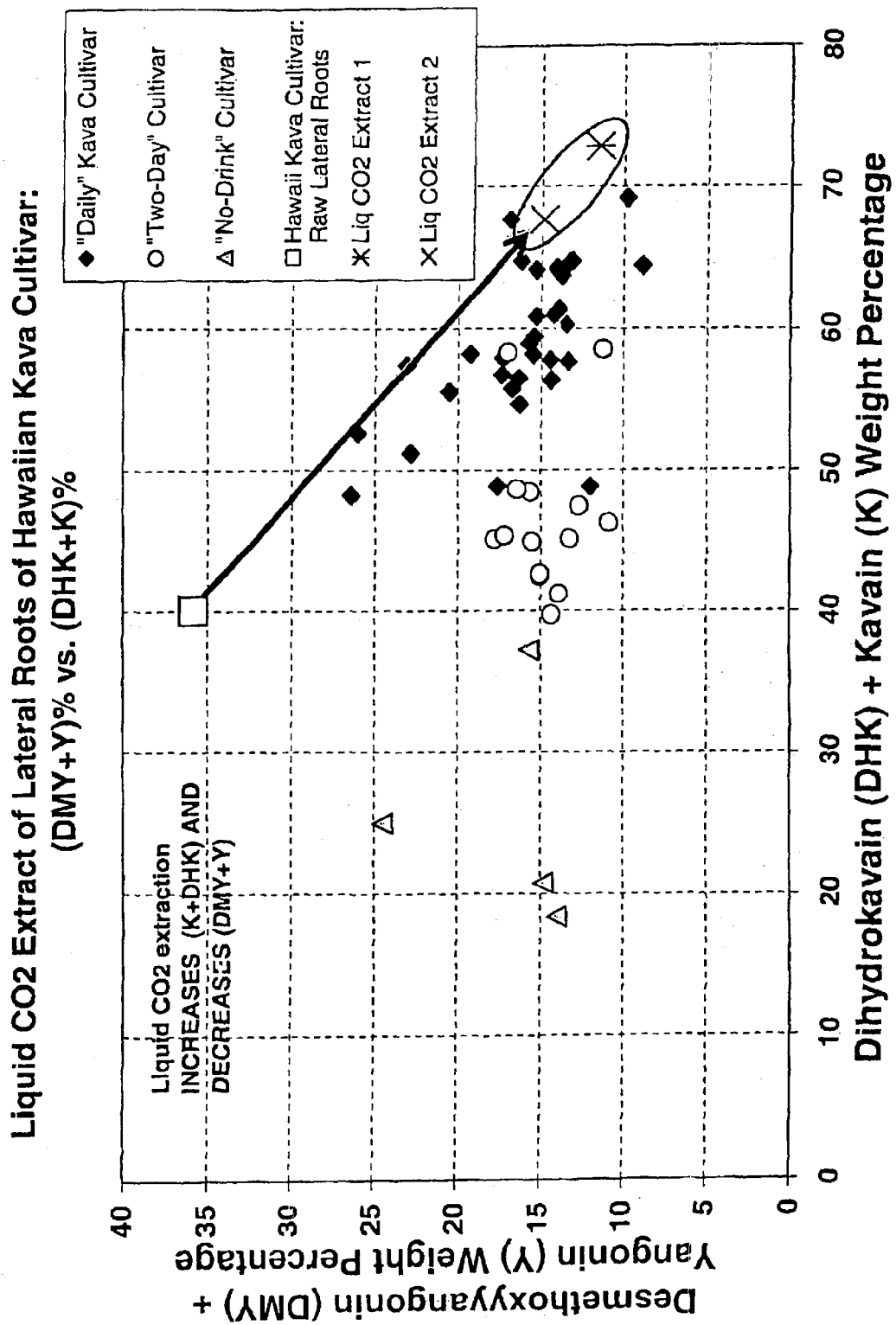
Figure 7:
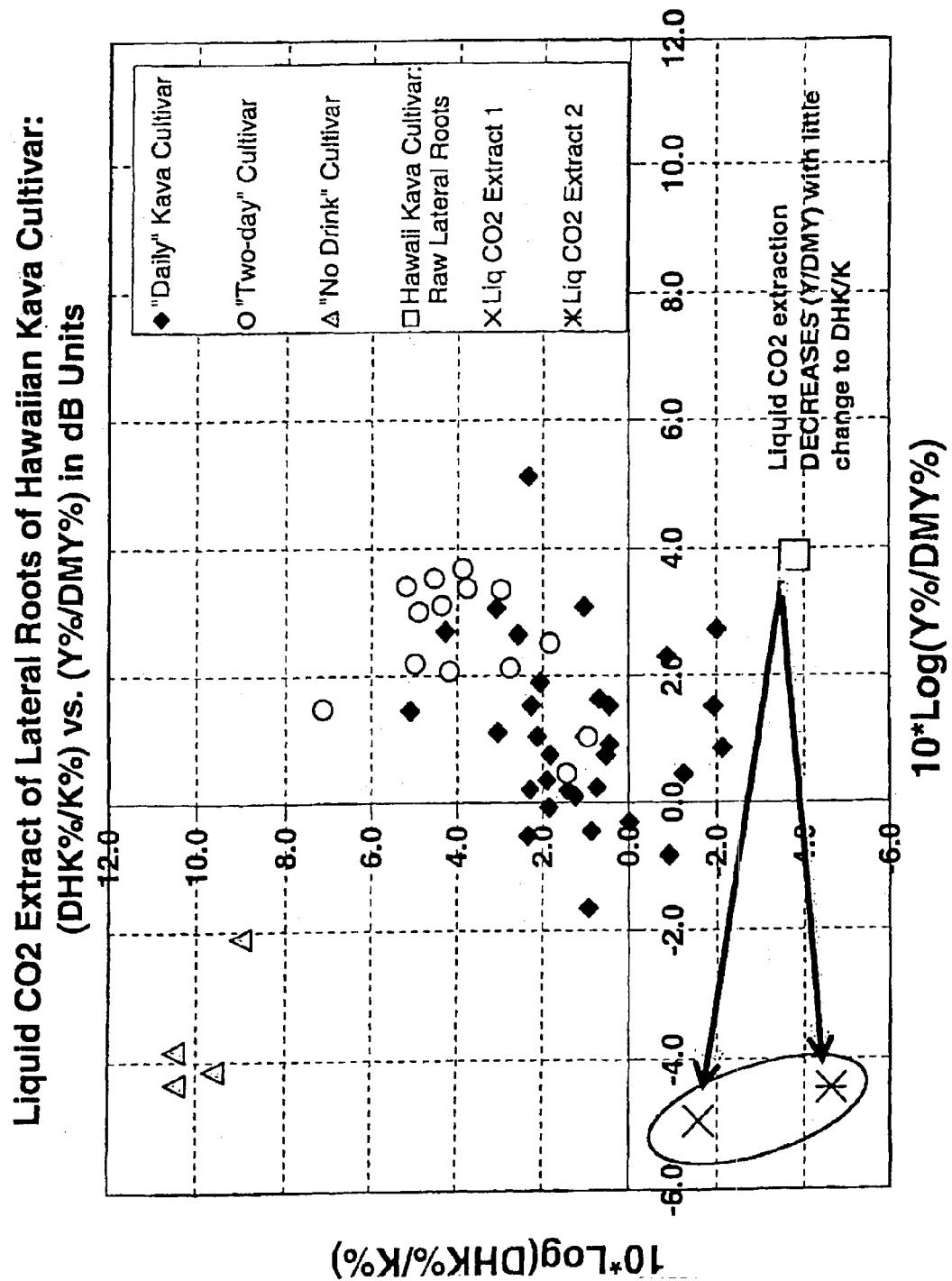

FIG. 3 is a map of average DHK/K vs. Y/DMY concentration ratios (in dB) for 1) lateral roots of the five different usage classes of Vanuatu kava cultivars, 2) lateral roots of 26 Fijian kava cultivars, 3) Alden Botanica's Essence of Kava (or EoK) extract of Vanuatu kava, and 4) Schwabe's Laitan kava extract. The DHK/K vs. Y/DMY map in FIG. 3 is effective in separating the five classes of Vanuatu kava cultivars, the Fijian kava cultivars, EoK, and Laitan. The average for the Fijian kavas falls in the fourth quadrant (DHK<1 and Y/DMY>1), in contrast to the averages for the D, C, M, and T Vanuatu kava cultivars in the first quadrant (DHK>1 and Y/DMY>1), and the average for the N Vanuatu kava cultivars in the second quadrant (DHK>1 and Y/DMY<1). Although EoK is made from Vanuatu kava, the composition is about 20% lateral roots and 80% rhizome. The high percentage of rhizome in EoK could explain why its DHK/K ratio is less than 1 because K tends to dominate in the rhizome. The M %+DHM % for EoK is 21%, which is characteristic of a Vanuatu Daily kava. The lateral root and rhizome compositions in Laitan are not known, and so it is difficult to suggest a reason for its DHK/K vs. Y/DMY mapping. However, its M %+DHM % of 34% is closer to the average M %+DHM % for Vanuatu Custom, Medicinal and/or Two-day kava cultivars and the average for Fijian kava cultivars. The high M %+DHM % of Laitan relative to that for EoK implies that Laitan will have a more muscle relaxing effect and a higher probability of inducing nausea.

As will be appreciated, there are many kava cultivars that contain kavalactone distributions which are not well suited for consumption. In order to generate a kava product, such as a paste or a dry flowable powder for use in fast dissolve tablet and other applications, raw kava root is processed to produce a kava paste, oil or resin (collectively referred to herein as "paste") that contains the kavalactones in the desired proportions, such as a distribution profile that corresponds to the most preferred Vanuatu one day cultivars. The paste can then be further processed, e.g., to produce a refined paste and/or a flowable powder. Preferred techniques are discussed below. These products generally can be referred to as a processed kava products.

As an initial step, the kava itself must be harvested, dried, and ground to size. The active kavalactones are most prevalent in the lateral roots of the plant. Various different cultivars are conventionally used, including but not limited to Isa, Mahakea, Moi, Papa Eleele, Borogu, Ahine, Kelaï, Palisi, Puna Green, Hanakapiai, Hiwa, Spotted Hiwa, Nene, SIG, Apu Awa, Alia, Melomelo, and Pia. Each cultivar has a typical concentration of the various kavalactones resulting in different effects from ingesting the root or a root extract. The harvested roots are preferably dried to a moisture content of between 3% and 10%, most preferably around 5%, and then ground to a particle size suitable for subsequent processing. A typical particle size is between about 60 mesh to about 300 mesh, which correlates to about 250μ to about 50μ, respectively, and preferably to between about 100μ and about 75μ.

The powdered kava root is then processed to produce a kava paste using techniques described below. In a preferred technique, the kava is processed using $CO_2$ in the liquid phase, but supercritical phase $CO_2$ extraction can be used. A solvent modifier, such as ethyl alcohol or refrigerant chemicals, can be added. Preferably, prior to the primary extraction steps, the feedstock is initially processed by subjecting it to a high pressure carbon dioxide environment followed by a rapid decompression. This compression-decompression process advantageously results in a substantially higher kavalactone yield than achieved without the decompression step.

The paste can then be further processed to produce a flowable powder. Although a paste made according to the present invention is preferably used, kava pastes produced using various alternative techniques can alternatively be used. Such methods include those disclosed in Published PCT Application WO 00/72861 to Martin et al. entitled "Pharmaceutical Preparations of Bioactive Substances Extracted from Natural Sources" and in U.S. Pat. No. 5,512,285 to Wilde entitled "Fragrance Extraction," the entire contents of which are both expressly incorporated by reference.

In a specific implementation of the method for producing the kava paste, the powdered dried root is placed in a stainless steel vessel and preprocessed by pressurizing the vessel with $CO_2$ to between about 1100 psi and about 4500 psi, preferably at least about 1800 psi, at a temperature of between about 10° C. and about 60° C., and preferably between about 15° C. and about 20° C. It is not required that the pressures reach the critical point of $CO_2$ (1100 psi and 31° C.) during this stage. After the desired pressure is reached and held for a period of time, ranging from continuous flow to fill and hold, where the hold time can vary from between about 5 minutes to about 60 minutes, the pressure in the extraction vessel is rapidly and substantially reduced, preferably to a level at or near one atmosphere. This preprocessing, while not necessary, allows for a higher efficiency of extraction in the subsequent processing steps.

As noted above, various extraction steps can be used to prepare the refined kava paste from a starting material. The particular techniques and solvents used are selected, to some extent, based on the moisture content present in the feedstock and on user preference. A specific factor that should be considered is the relative concentrations of the various kavalactones that is desired in the final product. For example, it can be beneficial to substantially reduce the amount of particular kavalactones in the extract which may cause interaction with various prescription drugs or cause various negative effects, while retaining high relative percentages of other kavalactones.

After the preferred decompression processing step is performed, the root contained within the stainless steel vessel is then processed to produce the kava extract paste. Various extraction processes (with or without the decompressive preprocessing) can preferably be used, with liquid $CO_2$ being the most preferred technique. The processes are preferably used in the alternative but two or more processes could be combined if desired. The processes are:

(1) $CO_2$ in the supercritical fluid phase.

(2) $CO_2$ in the liquid phase.

(3) $CO_2$ in the supercritical phase in combination with added ethyl alcohol as a modifier which is added in the range of 2% to 15%, and preferably between 2% and 10% based on the total mass.

(4) $CO_2$ in the liquid phase in combination with ethyl alcohol as a modifier which is added in the range of 2% to 15% and preferably between 2% and 10% based on the total mass.

(5) Refiigerant chemicals such as hydrofluorocarbons (HFCs), hydrochlorofluorocarbons (HCFCs), and/or chlorofluorocarbons (CFCs) such as: HFC-23, HFC-32, HFC-125, HFC-134a, HFC-143a, HFC-152a, R-404a, R-407c, R-410a, HCFC-22, HCFC-123, HCFC-141b, HCFC-142b, R-502, R-11, R-12, and R-113. A more complete listing of suitable refrigerant chemicals is in Table 2. These refrigerants are widely available from various chemical manufacturers and suppliers.

The selection of one extraction procedure over another depends on the objectives of the extraction, the kavalactone concentration profile of the raw starting material and the desired concentration profile of the extract end product. In order to extract the largest quantity of kavalactones in the aggregate, supercritical $CO_2$ extraction generally provides the best results. To alter or adjust the kavalactone profile, liquid $CO_2$ extraction techniques are more suitable. However, a carefully controlled supercritical $CO_2$ process may also be used. A gaseous $CO_2$ process may also be suitable under certain circumstances.

For example, if a starting kava feedstock has a kavalactone concentration profile (specified as weight percentages of the individual kavalavctones) that is relatively low in (K+DHK) and relatively high in both (M+DHM) and (DMY+Y), and a kava product is desired that is relatively high in (K+DHK) and relatively low in both (M+DHM) and (DMY+Y), then the $CO_2$ extraction in the liquid phase becomes the preferred process. The figures discussed below illustrate how liquid $CO_2$ extraction transformed the kavalactone concentration profile of the starting materials. In summary, the above extraction procedures provide maximum flexibility in starting with any kava raw product to obtain and extract end product with a specific kavalactone concentration profile.

In a first embodiment of the process, $CO_2$ is used in the supercritical phase to perform the extraction step. The pressure is held at a pressure and temperature regime that between about 1100 psi and about 8000 psi and at a temperature between about 31° C. and about 80° C. During the process the extractable material is collected within a stainless steel collection vessel that could be the same one as that used in the first "low pressure" extraction step, and the supercritical $CO_2$ can either be recycled for future use or vented into the atmosphere. The solvent-to-feed ratio increases as the pressure and temperature of the supercritical $CO_2$ is lowered. It has been found that when the material is processed at a pressure of about 8000 psi and a temperature of about 80° C., all extractable material is obtained after a solvent-to-feed ratio of 8 is achieved.

In a second, most preferred, embodiment, $CO_2$ in the liquid phase is used to perform the extraction step. Since the $CO_2$ is in the liquid phase, the extraction temperature can not exceed about 31° C., however the pressure can rise to about 8000 psi. Conversely, the pressure can be maintained below about 1100 psi and the temperature can be varied from about 5° C. up to about 70° C. During this process the extractable material is collected within the stainless steel collection vessel (which could be the same one as that used in a first "low pressure" extraction step). The liquid $CO_2$ can either be recycled for future use or vented into the atmosphere.

In a particular example of liquid $CO_2$ extraction and fractionation, $CO_2$ at a pressure between about 1100 and about 1800 psi is used at a temperature of between about 5° C. and about 20° C. The low temperature during extraction is controlled via a recirculating chiller plumbed to jacketed extractors, and the pressure within the extraction vessel is controlled via a back pressure regulator. Because of preferential absorption, and as discussed more fully below with respect to FIGS. 4–7, the kavalactone profile of the dissolved kava can be substantially different from the profile of the source kava.

The extract-laden fluid emanating from the extractor is then collected. A single collection vessel can be used or the fluid can be sequentially processed using multiple collecting vessels to allow for further refinement of the kava extract. In a particular example, the liquid is first heated, e.g., by using a heat exchanger, to a temperature between about 30° C. and about 37° C. The vessel into which the fluid is deposited is also maintained at the same temperature. A valve, such as a back pressure regulator situated just upstream of the collection vessel, can be used to allow the fluid to flow into the vessel at the set pressure. An additional back pressure regulator situated at the outlet of the first collection vessel can be used to maintain the first collection vessel at a pressure lower than that of the incoming fluid.

Maintaining the first collection vessel at a pressure of between about 1000 to about 1200 psi introduces a 100 psi to 800 psi pressure drop in the collection vessel relative to the fluid entering the collection vessel. The increase in temperature and decrease in pressure creates conditions that are not conducive to keeping the kavalactones, and kavain and dihydrokavain in particular, in solution. As a result, the kavalactones precipitate out of solution and can be collected in the collection vessel.

A second and third collection vessel can be situated in series with the first collection vessel such that a generally constant pressure in the two vessels of between about 1000 psi and about 1200 psi is maintained. However the temperature of each collection vessel increases so that, for example, the second collection vessel is maintained at a temperature above that of the first collection vessel, such as between about 35° C. and about 45° C., and the third collection vessel is maintained at a temperature above that of the second collection vessel, such as between about 40° C. and about 50° C.

In a third embodiment, $CO_2$ is used in the supercritical phase to perform the second extraction step with the addition of ethyl alcohol as a solvent modifier. The conditions are maintained identical to that described in (1) with the addition of ethyl alcohol at about 2% to about 15% and preferably between about 2% and about 10% of ethyl alcohol content by total mass. During the process the extractable material is collected within a stainless steel collection vessel which can be the same vessel as used in the first "low pressure" preprocessing step, and the supercritical $CO_2$ can either be recycled for future use or vented into the atmosphere. In this embodiment the extract will contain ethyl alcohol that can be removed in subsequent processing steps. The addition of ethyl alcohol increases the polarity of the solvent, resulting in enhanced extraction of the kavalactones with higher polarity, such as methysticin and dihydromethysticin, relative to the other kavalactones in the source material.

In a fourth embodiment, the conditions are generally the same as in the third embodiment but liquid $CO_2$ is used instead of supercritical $CO_2$.

In a fifth embodiment, refrigerant chemicals, such as HFCs, HCFCs, and CFCs, are used in the liquid phase to perform the extraction step. A selection of suitable HFCs, HCFCs, and CFCs appears in Table 2. During the extraction, the refrigerant chemical(s) are maintained in the liquid state and the pressure is kept below about 400 psi. Because of the comparatively low pressure, the extraction is varied primarily by temperature. Preferably, the temperature is maintained at between about 20° C. and about 70° C. and, in order to ensure suitable control and predictability, to within about ±0.1° C. of a target temperature. The refrigerant chemicals pass through the stainless steel extraction vessel containing the powdered root material and the extract-laden liquid is deposited into a stainless steel collection vessel (which can be the same one as that used in the preprocessing step). The refrigerant chemical of choice can be reclaimed via collection of the refrigerant chemical in its vapor state and subsequent pressurization into the liquid state. This is, in effect, a distillation process that leaves behind the root extract while recovering the refrigerant chemical as a liquid. The refrigerant chemical can then be re-cycled through the same mass of powdered root to repeat the process until all extractable material is removed from the powdered root or, leveraging changes in temperature and extraction solvent, until the extract has a desired kavalactone concentration.

The above-discussed processing steps will produce a kava root extract as a viscous oil, resin, or paste. According to one aspect of the invention, the preferential and/or differing rates of extraction of the various kavalactones in the feedstock for different solvents and extraction methods can be leveraged to produce a final refined kava product that has a relative kavalactone concentration meeting predefined specifications, even when those specifications may differ considerably from the concentrations present in the input kava feedstock.

Multiple extraction steps can be performed. In addition, and although not necessary, extraction can also be performed during the compression-decompression preprocessing step to selectively alter various kavalactone concentrations.

According to a particular aspect of the invention, an improved paste extract can be produced by performing an additional extraction step comprising use of supercritical $CO_2$ as a mobile phase combined with an adsorbent material such as that used for solid-phase extractions (SPE) and/or diatomaceous earth. The bonded materials used as silica sorbents include but are not limited to: C18 (Octadecyl), C8 (Octyl), C2 (Ethyl), CH (Cyclohexyl), PH (Phenyl), and CN (End-capped Cyanopropyl). In operation, the extract paste material obtained by the initial processing, such as via the methods discussed above, is mixed with the SPE bonded phase in a ratio of about 5:1 to about 1:1 (SPE bonded phase to root extract) by mass to produce a mixture having a doughy consistency. The mixture is then placed in an extraction vessel. Fractions can then be collected over time by pressurizing the vessel to between about 1100 psi and about 8000 psi and a temperature between about 31° C. and about 80° C. The material that elutes from this fractionation can be segregated from each other by using multiple stainless steel collection vessels. Each fraction will generally have a different percentage of kavalactones, as well as a unique distribution of kavalactones that is distinct from that seen in the original root material. Typically, the percentages of kavain and dihydrokavain are increased relative to the other kavalactones in the extract.

As will be appreciated, the time during which a solvent is allowed to flow over the kava feedstock can also effect the ratio of the final product since, for example, even a solvent that extracts a particular kavalactone slowly may eventually extract all of that kavalactone if sufficient time has passed. The particular amount of time to allow the solvent to operate before extraction of dissolved material from the solvent begins is dependent on the kavalactone distribution of the feedstock, the different rates at which the solvent extracts each of the kavalactones, and the desired kavalactone profile of the kava extract. Given the information presented herein, one of ordinary skill in the art, using only routine experimentation can select an appropriate time to terminate the extraction process.

The composition of a kava product can be described in a variety of ways. In accordance with the present invention, several parameters are defined which can be used to describe the composition of a kava extract:

1) Combined weight percentage of the six major alpha-pyrones: methysticin (M), dihydromethysticin (DHM), yangonin (Y), desmethoxyyangonin (DMY), kavain (K), and dihydrokavain (DHK);
2) Combined weight percentage of M and DHM;
3) Combined weight percentage of DHK and K;
4) Combined weight percentage of Y and DMY;
5) Ratio of the weight percentages of Y and DMY, i.e., Y/DMY;
6) Ratio of the weight percentages of DHK and K, i.e., DHK/K;
7) Combined weight percentage of flavokavain A and flavokavain B.

The first property is a rough indicator of the potency of the extract, e.g., if the extract has 0% total kavalactones it has no potency, and if it has 100% total kavalactones it is very potent. Properties 2–6 combine to define whether the kava extract can be classified in the "Daily" or "non-daily" categories, such as "Two-Day" and "No Drink". Property 7 is an indicator of the amount of flavokavains in the extract, Flavokavains are flavanoids specific to the kava plant. Flavanoids in general are anti-oxidants.

A most preferred kavalactone distribution for a kava extract, such as in a kava paste or a dry flowable power for use in oral delivery has a combination of the following properties:

1) Total weight percentage of M+DHM+Y+DMY+DHK+K ranges from a minimum of about 20% to a maximum of about 90%;
2) Combined M+DHM weight percentage ranges from a minimum of about 15% or lower to a maximum of about 29%;
3) Combined weight percentage of DHK and K ranges from a minimum of about 50% to a maximum of about 70%–80%;
4) Combined weight percentage of Y and DMY ranges from a minimum of about 5% to a maximum of about 25%;
5) Ratio of Y weight percentage to DMY weight percentage, expressed as the logarithmic function $10*LOG_{10}(Y/DMY)$ in dB units, ranges from a minimum of about –1 to a maximum of about 2;
6) Ratio of DHK weight percentage to K weight percentage, expressed as the logarithmic function $10*LOG_{10}(DHK/K)$ in dB units, ranges from a minimum of about –4 to a maximum of about 1; and
7) Combined weight percentage of flavokavain A and flavokavain B ranges from a minimum of about 0.3% to a maximum of about 3%.

The value of these properties for a sample of a processed kava product can be determined using conventional analytical techniques, such as HPLC-UV-S (High Performance Liquid Chromatography with Ultra-Violet detection (254 nm) and Chemical Standards), or HPLC-Electrospray-Mass Spectrometry.

Property 1 indicates that in order to have a potent product, such as a tablet, it should have a minimum of about 20% kavalactones by weight, and a maximum of about 90% kavalactones by weight. Property 7 indicates that the weight percentage of the flavokavains should be about 0.3% to about 3%, which values are typical for unprocessed kava. However, in conventional processed kava extracts, the flavokavains tend to be removed, either deliberately or due to processing effects.

Properties 2–4 combine to define extracts with a kavalactone distribution typical of a "Daily" kava cultivar found in Vanuatu. Properties Attributes 2, 5 and 6 also combine to define extracts with a kavalactone distribution typical of a "Daily" kava cultivar found in Vanuatu. The range of properties 2–7 are taken from the values measured for "Daily" kava cultivars found in Vanuatu.

According to a preferred particular embodiment, a processed kava product produced according to the invention comprises less than about 15% of the combination of methysticin and dehyromethysticin, less than about 8% of the combination of yangonin and desmethooxyyangonin, and greater than about 70% of the combination of kavain and dihydrokavain. A similar kavalactone composition comprises up to about 7% methysticin, up to about 5% dehyromethysticin, up to about 1 % yangonin, up to about 4% desmoxyyangonin, and greater than about 38% kavain.

In an alternative embodiment, the product is not limited to the production method discussed heretofore. For instance, the product may be synthetically produced by combining the individual kavalactones in their desired weight ratios. In this embodiment, the resulting material preferably has a kavalactone profile having at least one of the following characteristics: a) a combined weight percentage of M and DHM less than about 15% of the total weight of the profile, b) a combined weight percentage of DMY and Y less than about 8% of the total weight of the profile and c) a combined weight percentage of K and DHK greater than about 70% by weight of the kavalactone profile. In this embodiment, M is less than about seven percent by weight of the kavalactone profile, DHM is less than about five percent by weight of the kavalactone profile, DMY is less than about four percent by weight of the kavalactone profile, Y is less than about one percent by weight of the kavalactone profile, DHK is greater than about fifty percent by weight of the kavalactone profile or K is greater than about thirty-eight percent by weight of the kavalactone profile. Specifically, a) M is in the range of about 2.6 percent to about 4.8 percent by weight of said kavalactone profile; b) DHM is in the range of about 8.7 percent to about 13 percent by weight of said kavalactone profile; c) K is in the range of about 28 percent to about 39 percent by weight of said kavalactone profile; d) DHK is in the range of about 30 percent to about 52.4 percent by weight of said kavalactone profile; e) Y is in the range of about 0 percent to about 1.4 percent by weight of said kavalactone profile; and 0) DMY is in the range of about 8.4 percent to about 11.8 percent by weight of said kavalactone profile. Furthermore, this material may have a kavalactone profile with a ratio of DHK to K by weight of less than about −4 dB or a ratio of Y to DMY by weight of less than about −5 dB.

The material described herein may also be characterized as having a kavalactone profile as follows: a) a combined weight of M and DHM less than about 20% of the kavalactone profile, a combined weight of Y and DMY less than about 56% and the combined weight of DMY and Y is present in a weight percentage equal to about −2.78 multiplied by the weight percentage of the combined weight of M and DHM plus about 56%; b) a combined weight of M and DHM less than about 60% of the kavalactone profile, a combined weight of Y and DMY less than about 13% and the combined weight of DMY and Y is present in a weight percentage equal to about −0.22 multiplied by the weight percentage of the combined weight of M and DHM plus about 60%; or c) a combined weight of M and DHM less than about 64% of the kavalactone profile, a combined weight of K and DHK less than about 79% and the combined weight of K and DHK is present in a weight percentage equal to about −1.23 multiplied by the weight percentage of the combined weight of M and DHM plus about 79%. Finally, the material described herein may be characterized as having a kavalactone profile having a weight ratio of K to DHK less than about −4.313 multiplied by the weight ratio of Y to DMY minus about 10 dB.

In the extraction methods discussed above, the desired kavalactones were extracted from a source material, such as ground kava root or a pre-processed kava paste, and the remainder contained the undesirable materials. The opposite technique can also be used. In particular, a kava source material can be processed using a solvent that preferentially extracts undesired kavalactones, such as methysticin and dehyromethysticin, faster than other, more desired kavalactones. The material remaining in the extraction vessel would then be collected and cold have the desired altered kavalactone profile. It has been determined that the extraction rate of methysticin and dehyromethysticin increases with increasing polarity of the extract and that certain refrigerant solvents, such as R22, can extract these undesirable kavalactones at a sufficiently greater rate than remaining kavalactones to allow this alternative refinement technique to be used. The specific extraction environments, rates of extraction, and solvent used depends on the starting profile of the source material and the degree of profile change desired. Specific solvent and environmental attributes can be determined by those of ordinary skill in the art using no more than routine experimentation typical for adjusting a process to account for, e.g., variations in the attributes of starting materials that is to be processed to produce an output material that has specified attributes.

A kava paste extract, such as discussed above, can be processed to produce consumable items, for example, by mixing it in a food product or in a capsule, or providing the paste itself for use as a dietary supplement, with sweeteners and flavors added as appropriate. However, a paste extract of this type can be difficult to process because it does not flow well and may therefore not be well suited for processing by various types of high speed machinery.

According to a further aspect of the invention, the kava paste extract discussed above (or a kava paste produced using other techniques) can be further processed to produce a dry, flowable kava powder. The powder can be used as a dietary supplement that can be added to various edible products. The powder is also suited for use in a rapid dissolve tablet.

According to a particular aspect of the invention, the kava extract powder is produced to have a kavalactone distribution that is particularly well suited for delivery in the oral cavity of human subjects, e.g., via a rapid dissolve tablet. Preferably, the desired distribution properties are achieved by adjusting the extraction process to take advantage of the differing extraction rates of the various kavalactones according to type of extraction method and the operating parameters used. Although this technique may not result in an extract that contains substantially all of the kavalactones from a sample (as is the goal of conventional extraction processes), the desired ratios can be achieved without having to perform extraction of individual kavalactones, e.g., through chromatography, and then a subsequent recombination of the individual extracts.

In one embodiment of a method for producing the kava powder, the extract paste is mixed with a suitable solvent, such as ethyl alcohol or water, along with a suitable food-grade carrier material, such as maltodextrin, dextrose, or starch and the mixture is spray air-dried using conventional techniques to produce a powder having grains of very small kava extract particles combined with the food-grade carrier material.

In a particular example, a kava extract paste, preferably about 60% to about 80% total kavalactones by weight, is mixed with about twice its weight of a food-grade carrier, such as maltodextrin having with an average particle size of between about 100 to about 150 micrometers and an ethyl alcohol solvent using a high shear mixer. Inert carriers, such as silica, preferably having an average particle size on the order of about 1 to about 50 micrometers, can be added to improve the flow of the mixture. Preferably, such additions are up to about 2% by weight of the mixture. The amount of ethyl alcohol used is preferably the minimum needed to form a solution with a viscosity appropriate for spray air-drying. Typical amounts are in the range of between about 5 to about 10 liters per kilogram of paste. The solution of kava extract, maltodextrin and ethyl alcohol is spray dried to generate a powder with an average particle size comparable to that of the starting carrier material and a kavalactone content of about 20% to about 35% by weight.

In a second embodiment, the kava extract paste and a food-grade carrier, such as magnesium carbonate, a whey protein, or maltodextrin, are dry mixed, followed by mixing in a high shear mixer containing a suitable solvent, such as ethyl alcohol or water. The mixture is then dried via freeze drying or refractive window drying. In a particular example, kava extract paste comprising on the order of about 60% to about 80% total kavalactones by weight is combined with about one and one-half times by weight of the paste of a food-grade carrier, such as magnesium carbonate, having an average particle size of about 20 to about 100 micrometers. Inert carriers, such as silica, and preferably having an average particle size of about 1 to about 50 micrometers can be added, preferably in an amount up to 2% by weight of the mixture, to improve the flow of the mixture. The magnesium carbonate and silica are then dry mixed in a high-speed mixer, similar to a food processor-type of mixer, operating at 100's of rpm. The kava extract paste then is heated until it flows like a heavy oil. Preferably, it is heated to at least about 50° C. The heated kava paste/oil is then added to the magnesium carbonate and silica powder mixture that is being mixed in mixer.

The mixing of the kava paste/oil and the magnesium carbonate and silica is continued preferably until the particle sizes are in the range of between about 250 micrometers to about 1 mm. Between about two to ten liters of cold water (preferably at about 4° C.) per kilogram of paste is introduced into a high shear mixer. The mixture of kava extract paste, magnesium carbonate and silica is the introduced slowly or increments into the high shear mixer while mixing. An emulsifying agent, such as carboxymethylcellulose can also be added to mixture if needed. Sweetening agents can also be added at this stage if desired, such as up to about 5% by weight. Alternatively, extract of *Stevia rebaudiana*, a very sweet-tasting dietary supplement, can be added instead of, or in conjunction with, a specific sweetening agent. (For simplicity, *Stevia* will be referred to herein as a sweetening agent.) After mixing is completed, the mixture is dried using freeze-drying or refractive window drying. The resulting dry flowable powder of kava extract, magnesium carbonate, silica and optional emulsifying agent and optional sweetener has an average particle size comparable to that of the starting carrier material and a kavalactone content of about 20% to about 35% by weight.

According to another embodiment, kava extract paste that is on the order of about 60% to about 80% total kavalactones by weight is combined with approximately an equal weight a food-grade carrier, such as whey protein, preferably having an average particle size of between about 200 to about 1000 micrometers. Inert carriers, such as silica preferably having an average particle size of between about 1 to about 50 micrometers, or carboxymethylcellulose, preferably having an average particle size of between about 10 to about 100 micrometers, can be added to improve the flow of the mixture. Preferably, this addition is no more than about 2% by weight of the mixture.

The whey protein and inert ingredient are then dry mixed in a food processor-type of mixer that operates at 100's of rpm. The kava extract paste is heated until it flows like a heavy oil. Preferably, it is heated to at least 50° C. The heated kava paste/oil is then added to the whey protein and inert carrier that is being mixed in the food processor-type mixer. The mixing of the kava paste/oil and the whey protein and inert carrier is continued until the particle sizes are in the range of about 250 micrometers to about 1 mm. Next, 2 to 10 liters cold water (preferably about 4C) per kilogram of paste is introduced into a high shear mixer. The mixture of kava extract paste, whey protein and inert carrier is preferably introduced slowly or in incremental amounts with the high shear mixer while mixing. Sweetening agents or other sweet-tasting additives of up to about 5% by weight, such as *Stevia*, can be added at this stage if desired.

After mixing is completed, the mixture is dried using freeze-drying or refractive window drying. The resulting dry flowable powder of kava extract, whey protein, inert carrier and optional sweetener has an average particle size of about 150 to about 700 micrometers and a kavalactone content of about 20% to about 35% by weight.

In a third embodiment, the kava extract paste is dissolved in a supercritical fluid, which is then adsorbed onto a suitable food-grade carrier, such as maltodextrin, dextrose, or starch. Preferably, supercritical $CO_2$ is used as the solvent. Specific examples include starting with a kava extract paste that is on the order of about 60% to about 80% total kavalactones by weight and adding from 1 to one one-half times the paste by weight of a food-grade carrier, such as maltodextrin, and having an average particle size of between about 100 to about 150 micrometers. This mixture is placed into a chamber containing mixing paddles and which can be pressurized and heated. The chamber is pressurized with $CO_2$ to a pressure in the range of between about 1100 to about 8000 psi and set at a temperature in the range of between about 20° to about 100° C. The exact temperature and pressure is selected to place the $CO_2$ in a supercritical fluid state.

Once the $CO_2$ in the chamber is in the supercritical state, the kava extract paste is dissolved. The mixing paddles agitate the carrier powder so that it has intimate contact with the supercritical $CO_2$ that contains the dissolved kava extract paste. The mixture of supercritical $CO_2$, dissolved kava extract paste and the carrier powder is then vented through an orifice in the chamber so that it undergoes explosive decompression into a collection vessel which is at a pressure and temperature that does not support the supercritical state for the $CO_2$. The $CO_2$ is thus dissipated. The resulting powder in the collection vessel is the carrier powder impregnated with the kava extract paste. The powder has an average particle size comparable to that of the starting carrier material and a kavalactone content of between about 20% to about 40% by weight. The resulting powder is dry and flowable. If needed, the flow characteristics can be improved by adding inert ingredients to the starting carrier powder, such as silica at up to about 2% by weight as discussed above.

Once a dry kava powder is obtained, such as by the methods discussed herein, it can be distributed for use, e.g., as a dietary supplement or for other uses. In a particular embodiment, the powder is mixed with other ingredients to form a tableting composition of powder which can then be formed into tablets. In a particular embodiment, the tableting powder is first wet with a solvent comprising alcohol, alcohol and water, or other suitable solvents, in an amount sufficient to form a thick doughy consistency. Suitable alcohols include, but are not limited to, ethyl alcohol, isopropyl alcohol, denatured ethyl alcohol containing isopropyl alcohol, acetone, and denatured ethyl alcohol containing acetone. The resulting paste is then pressed into a tablet mold. An automated molding system, such as described in U.S. Pat. No. 5,407,339 can be used. The tablets are then removed from the mold and dried, preferably by air-drying for at least several hours at a temperature high enough to drive off the solvent used to wet the tableting powder mixture, typically between about 70° to about 85° F. The tablets can then be packaged for distribution.

A wide variety of tablet formulations can be made. Preferably, the tablet has a formulation that results in a rapid dissolution or disintegration in the oral cavity. The tablet is preferably of a homogeneous composition that dissolves or disintegrates rapidly in the oral cavity to release the kava extract content over a period of about 2 seconds or less to about 60 seconds or more, preferably about 3 to about 45 seconds, and most preferably between about 5 to about 15 seconds.

Various rapid-dissolve tablet formulations known in the art can be used. Representative formulations are disclosed in U.S. Pat. Nos. 5,464,632, 6,106,861, and 6,221,392, the entire contents of which are expressly incorporated by reference herein. A particularly preferred tableting composition or powder contains about 10% to about 60% by weight of the kava extract powder and about 30% to about 60% of a water-soluble diluent. Suitable diluents include lactose, dextrose, sucrose, mannitol, and other similar compositions. Lactose is a preferred diluent but mannitol adds a pleasant, cooling sensation and additional sweetness in the mouth. More than one diluent can be used. A sweetener can also be included, preferably in an amount of between about 3% to about 40% by weight depending on the desired sweetness. Preferred sweetening substances include sugar, saccharin, sodium cyclamate, aspartame, and *Stevia* extract, used singly or in combination, although other sweeteners could alternatively be used. Flavorings, such as mint, cinnamon, citrus (e.g., lemon or orange), can also be included, preferably in an amount between about 0.001% to about 1% by weight.

Typically, the kava extract added to the tablet has a golden color and it is considered unnecessary to include additional colorings. However, if a coloring is desired, natural and/or synthetic colors can be added, preferably in an amount of between about 0.5% to about 2% by weight.

Typically, this tableting composition will maintain its form without the use of a binder. However, if needed, various binders are suitable and can be added in an amount of between about 5% to about 15% or as necessary. Preferred binders are acacia or gum arabic. Alternative binders include sodium alginate, extract of Irish moss, panwar gum, ghatti gum, mucilage of isapol husks, carboxymethylcellulose, hydroxyethylcellulose, methylcellulose, polyvinylpyrrolidone, VEEGUM® (available from R.T Vanderbilt Co., Inc. of Norwalk, Conn.), larch arabogalactan, gelatin, Kappa carrageenan, copolymers of maleic anhydride with ethylene or vinyl methyl ether.

A tablet according to this aspect of this invention typically does not require a lubricant to improve the flow of the powder for tablet manufacturing. However, if it is so desired, preferred lubricants include talc, magnesium stearate, calcium stearate, stearic acid, hydrogenated vegetable oils, and carbowax in amounts of between about 2% to about 10% by weight.

Similarly, a disintegrant is not expected to be necessary to produce rapid dissolve tablets using the present tablet composition. However, a disintegrant can be included to increase the speed with which a resulting tablet dissolves in the mouth. If desired, between about 0.5% to about 1% by weight of a disintegrant can be added. Preferred disintegrants include starches, clays, celluloses, algins, gums, crosslinked polymers (including croscarmelose, crospovidone and sodium starch glycolate), VEEGUM® HV, agar, bentonite, natural sponge, cation exchange resins, aliginic acid, guar gum, citrus pulp, sodium lauryl sulphate in an amount of about 0.5% to about 1% of the total mass of the tablet.

It is also generally considered unnecessary to buffer the tablet composition. However, a buffer may be beneficial in specific formulations. Preferred buffering agents include mono- and di-sodium phosphates and borates, basic magnesium carbonate and combinations of magnesium and aluminum hydroxide.

In a preferred implementation, the tableting powder is made by mixing in a dry powdered form the various components as described above, e.g., active ingredient (kava extract), diluent, sweetening additive, and flavoring, etc. An average in the range of about 10% to about 15% of the active extract of the active ingredient can be added to compensate for losses during subsequent tablet processing. The mixture is then sifted through a sieve with a mesh size preferably in the range of about 80 mesh to about 100 mesh to ensure a generally uniform composition of particles.

The tablet can be of any desired size, shape, weight, or consistency. The total weight of the kava extract in the form of a dry flowable powder in a single oral dosage is typically in the range of about 80 mg to about 600 mg. An important consideration is that the tablet is intended to dissolve in the mouth and should therefore not be of a shape that encourages the tablet to be swallowed. The larger the tablet, the less it is likely to be accidentally swallowed, but the longer it will take to dissolve or disintegrate. In a preferred form, the tablet is a disk or wafer of about ⅛ inch to about ½ inch in diameter and about 0.2 inch to 0.08 inch in thickness, and has a weight of between about 160 mg to about 1,200 mg. In addition to disk, wafer or coin shapes, the tablet can be in the form of a cylinder, sphere, cube, or other shapes. For example, the tablet can be formed into the general shape of a kava plant leaf. Although the tablet is preferably homogeneous, the tablet may alternatively be comprised of regions of powdered kava extract composition separated by non-kava extract regions in periodic or non-periodic sequences, which can give the tablet a speckled appearance with different colors or shades of colors associated with the kava extract regions and the non-kava extract regions An exemplary 250 mg tablet contains about 125.0 mg powdered kava extract, about 12.5 mg extract of *Stevia*, about 35.5 mg carboxymethylcellulose, and about 77.0 mg lactose. An exemplary 350 mg tablet contains about 160.0 mg powdered kava extract, about 15.0 mg extract of *Stevia*, about 15.0 mg acacia, and about 160.0 mg lactose. Other formulations are also possible.

Although the extraction techniques are discussed herein in terms of kava, it should be recognized that the disclosed techniques can be adapted for use in forming an extract, in the form of a dry flowable powder or another form and containing compositions extracted from other plant products, such as ginseng, cherry, lettuce, echinacea, mate, and areca. In addition, while the preferred rapid dissolved formulation is disclosed herein in the context of kava extract, the formulation can also be used to provide a rapid dissolve tablet containing additional or other active ingredients that can be provided in powder form, such as varieties of ginseng, cherry, lettuce, echinacea, mate, and areca

EXAMPLES

The following examples are illustrative of the nature of the present invention and are not to be regarded as limiting.

Example 1

This example describes the preparation of a kava extract having the properties shown in FIGS. 1–4 (i.e., properties typical of a "Daily" kava cultivar from Vanuatu). This process can be varied as needed and in accordance with the profile of the source kava and the desired kava profile of the extract.

About 30 lbs. of chopped and ground lateral roots of kava are added to a 32 liter extraction vessel. Pre-cooled liquid carbon dioxide (the pressurized liquid carbon dioxide was passed through a heat exchanger that was maintained at 0° C.) was pumped through the vessel at a pressure of 1800 psi. The carbon dioxide expanded and flashed into a gas, thus cooling the lateral root to approximately 10° C. The resultant temperature equilibrium of the effluent flowing from the extraction vessel was between 5° C. and 20° C. Approximately 500 lbs. of liquid carbon dioxide was passed through the lateral roots under pressure, but below the supercritical temperature. This extraction was high pressure liquid extraction. The extract laden liquid carbon dioxide was collected in a vessel that was at atmospheric pressure.

FIGS. 1–4, respectively, are plots of (DHK %+K %) vs. (M %+DHM %), (DMY %+Y %) vs. (M % DHM %), (DMY %+Y %) vs. (DHK %+K %), and $10*LOG_{10}(DHK/K)$ vs. $10* LOG_{10}(Y/DMY)$ for the appropriate values measured for "Daily", Two-Day "and "No Drink" kava cultivars from Vanuatu. The plots show the changes in the kavalactone profile introduced during processing according to the present invention. The plots show how the kavalactone profile of the processed product is shifted away from an undesirable profile to a more desired profile.

More generally, FIGS. 1–4 show how a raw kava product with a kavalactone distribution that is not typical of the preferred "Daily" kava can be processed to yield an extract with a kavalactone distribution more typical of the "Daily" kava. Note that the processing method simultaneously changes all Properties 2–6, discussed above, as well as increasing the total kavalactone weight percentage. In an optional step, the extract laden liquid carbon dioxide was collected into a cascade of three different vessels that are maintained at different temperatures and under pressures so as to further altered the kavalactone profile of the extract collected in each vessel.

Example 2

A common kava feedstock was processed and passed through sequentially connected collection vessels containing different temperature and pressure environments to produce different extraction conditions. In particular, three vessels were used containing liquid, supercritcal and gaseous $CO_2$, respectively. The profile of the kava extracts at each stage of processing compared with the profile of the source. The first collection vessel was used for liquid $CO_2$ extraction. The vessel was pressurized to 1150 psi and maintained at 26.2° C. The extraction was performed at 1200 psi and 7° C. The second collection vessel was used for supercritical $CO_2$ extraction. The vessel was pressurized to 1150 psi and maintained at 33.5° C. The third collector was used for gaseous $CO_2$ collection. The collection vessel was pressurized to 850 psi and maintained between 20° C. and 30° C.

A comparison of the profile of the source feedstock and the profile of the extracts is shown in table 3, below:

TABLE 3

CHANGE IN KAVALACTONE PROFILE (in percentages)

| Kavalactone | Feed-stock | Profile in 1st extraction vessel | Profile in 2nd extraction vessel | Profile in 3rd extraction vessel |
| --- | --- | --- | --- | --- |
| Methysticin (M) | 19.7 | 13.9 | 4.8 | 2.6 |
| Dihydromethysticin (DHM) | 10.2 | 10.4 | 13.0 | 8.7 |
| Kavain (K) | 22.5 | 41.8 | 39.0 | 28.0 |
| Dihydrokavain (DHK) | 12.7 | 10.9 | 30.0 | 52.4 |
| Yangonin (Y) | 22.7 | 5.8 | 1.4 | 0.0 |
| Desmethoxyyangonin (DMY) | 12.3 | 17.3 | 11.8 | 8.4 |

There are three dramatic changes that have occurred. First, the combined M+DHM content has dropped from 29.9% to as low as 11.3%. Second, the combined K+DHK content has increased from 35.2% to as high as 80.4%. Third, the yangonin content has dropped from 22.7% to a non-detected level, effectively 0.0%. As will be appreciated, a careful choice of the temperature and pressure for each collector will result in controlled and preferential distributions of the kavalactones.

TABLE 2

| | Refrigerant chemicals | | | | | | | | |
| --- | --- | --- | --- | --- | --- | --- | --- | --- | --- |
| | HFC | | | | | | HFC mixed refrigerant | | |
| Product name | HFC-23 | HFC-32 | HFC-125 | HFC-134a | HFC-143a | HFC-152a | R-404A | R-407C | R-410A |
| Component | HFC-23 | HFC-32 | HFC-125 | HFC-134a | HFC-143a | HFC-152a | HFC-125/143a/134a | HFC-32/125/134a | HFC-32/125 |
| Chemical Formula | $CHF_3$ | $CH_2F_2$ | $CHF_2CF_3$ | $CH_2FCF_3$ | $CH_3CF_3$ | $CH_3CHF_2$ | 1 | 2 | 3 |

| | HCFC | | | | Mixed refrigerant with CFC | CFC | | |
| --- | --- | --- | --- | --- | --- | --- | --- | --- |
| Product name | HCFC-22 | HCFC-123 | HCFC-141b | HCFC-142b | R-502 | R-11 | R-12 | R-113 |
| Component | HCFC-22 | HCFC-123 | HCFC-141b | HCFC-142b | HCFC-22/CFC-115 (Azeotropic blend) | CFC-11 | CFC-12 | CFC-113 |
| Chemical Formula | $CHC_1F_2$ | $CHC_{12}CF_3$ | $CH_3CC_{12}F$ | $CH_3CC_1F_2$ | 4 | $CC_{13}F$ | $CC_{12}F_2$ | $CC_{12}FCC_1F_2$ |

1-$CHF_2CF_3/CH_3CF_3/CH_2FCF_3$(44/52/4 mass %)
2-$CH_2F_2/CHF_2CF_3/CH_2FCF_3$(23/25/52 mass %)
3-$CH_2F_2/CHF_2CF_3$(50/50 mass %)
4-$CHCIF_2/CC_1F_2CF_3$(48.8/51.2 mass %)

We claim:

1. A kava extract composition, comprising, extracted kavalactones consisting of a methysticin component that is less than about seven percent by weight of the total weight of extracted kavalactones, a dihydromethysticin component, a desmethoxyyangonin component, a yangonin component, a dihydrokavain component, and a kavain component.

2. The kava extract composition of claim 1, wherein the dihydromethysticin component is less than about five percent by weight the total weight of extracted kavalactones.

3. The kava extract composition of claim 1, wherein the desmethoxyyangonin component is less than about four percent by weight of the total weight of extracted kavalactones.

4. The kava extract composition of claim 1, wherein the yangonin component is less than about one percent by weight of the total weight of extracted kavalactones.

5. The kava extract composition of claim 1, wherein the dihydrokavain component is greater than about fifty percent by weight of the total weight of extracted kavalactones.

6. The kava extract composition of claim 1, wherein the kavain component is greater than about thirty-eight percent by weight of the total weight of extracted kavalactones.

7. The kava extract composition of claim 1, wherein the extracted kavalactones have a ratio of the dihydrokavain component to the kavain component, by weight, of less than about −4 dB.

8. The kava extract composition of claim 1, wherein the extracted kavalactone have a ratio of the yangonin component to the desmethoxyyangonin component, by weight, of less than about −5 dB.

9. The kava extract composition of claim 1, comprising,
a methysticin component that is in the range of about 2.6 percent to about 4.8 percent, by weight, of the total weight of extracted kavalactones;
a dihydromethysticin component that is in the range of about 8.7 percent to about 13 percent, by weight, of the total weight of extracted kavalactones;
a kavain component that is in the range of about 28 percent to about 39 percent, by weight, of the total weight of extracted kavalactones;
a dihydrokavain component that is in the range of about 30 percent to about 52.4 percent, by weight, of the total weight of kavalactones;
a yangonin component that is in the range of about 0 percent to about 1.4 percent, by weight, of the total weight of extracted kavalactones; and
a desmethoxyyangonin component that is in the range of about 8.4 percent to about 11.8 percent, by weight, of the total weight of kavalactones.

10. A kava extract composition, comprising, extracted kavalactones consisting of,
a first composition, comprising a methysticin component and a dihydromethysticin component, that is less than about sixty-four percent, by weight, of the total weight of extracted kavalactones;
a second composition comprising said desmethoxyyangonin component and said yangonin component, and
a third composition comprising a kavain component and a dihydrokavain component, that is less than about seventy-nine percent, by weight, of the total weight of extracted kavalactones.

11. The kava extract composition of claim 1, wherein the amount of the combined methysticin component and the dihydromethysticin component is less than about fifteen percent by weight of the total weight of the extracted kavalactones.

12. The kava extract composition of claim 1, wherein the amount of the combined desmethoxyyangonin component and the yangonin component is less than about eight percent by weight of the total weight of the extracted kavalactones.

13. The kava extract composition of claim 1, wherein the amount of the combined kavain component and the dihydrokavain component is greater than about seventy percent by weight of the total weight of the extracted kavalactones.

* * * * *